United States Patent [19]
Boutevin et al.

[11] Patent Number: 5,283,380
[45] Date of Patent: Feb. 1, 1994

[54] PROCESS FOR PREPARING AN ACTIVE TELOGEN

[75] Inventors: Bernard Boutevin, Montpellier, France; Gerald A. Gornowicz, Midland, Mich.

[73] Assignee: Dow Corning Corporation, Midland, Mich.

[21] Appl. No.: 76,527

[22] Filed: Jun. 11, 1993

[30] Foreign Application Priority Data

Jun. 15, 1992 [FR] France .................................. 92 07185

[51] Int. Cl.$^5$ ............................................. C07C 19/08
[52] U.S. Cl. ....................................................... 570/161
[58] Field of Search ........................................... 570/161

[56] References Cited

U.S. PATENT DOCUMENTS

3,006,973 10/1961 Hauptscheim ...................... 570/161
3,933,931 1/1976 Oda ..................................... 570/161

OTHER PUBLICATIONS

Chambers et al., J. Chem. Soc., 3779 (1961).
Hauptschein et al., J. Amer. Chem. Soc. 83 (1961) 2383.

*Primary Examiner*—Alan Siegel
*Attorney, Agent, or Firm*—Roger E. Gobrogge

[57] ABSTRACT

This invention relates to an improved method of preparing the active telogen $CF_3CFClI$. The process comprises reacting chlorotrifluoroethylene, iodine, and iodine pentafluoride in the presence of an aluminum bromide catalyst at a temperature above about 25° C.

8 Claims, No Drawings

PROCESS FOR PREPARING AN ACTIVE TELOGEN

BACKGROUND

The present invention relates to an improved method of preparing a telogen of the structure $CF_3CFClI$. The method involves reacting a mixture comprising iodine, iodine pentafluoride, and chlorotrifluoroethylene (CTFE) in the presence of an aluminum bromide catalyst for a time sufficient to form the telogen. The resultant telogen is advantageous for telomerizing fluorinated olefins.

Chambers et al. in J. Chem. Soc., 3779 (1961), teach the reaction of iodine with iodine pentafluoride to form iodine monofluoride. This reference also teaches that the iodine monofluoride can react with fluorinated olefins such as CTFE at room temperature without catalysts to form moderate yields (37%) of $CF_3CFClI$.

Hauptschein et al. in J. Amer. Chem Soc. 83 (1961) 2383, teach a catalyzed reaction of iodine and iodine pentafluoride with CTFE to form $CF_3CFClI$. The method described in this reference comprises a two step process in which iodine and iodine pentafluoride in a molar ratio of at least 2:1 were reacted in the presence of an aluminum metal/aluminum iodide catalyst at a temperature of 100°-175° C. to form iodine monofluoride. The iodine monofluoride was then reacted with CTFE in a second step at room temperature to form less than a 50% yield of the desired telogen.

The inventors herein have now discovered that by using the simple process and reactants of the present invention they can obtain good yields of $CF_3CFClI$.

SUMMARY OF THE INVENTION

The present invention relates to a novel method of making an active telogen of the structure $CF_3CFClI$. The method comprises reacting a mixture comprising iodine, iodine pentafluoride, and a stoichiometric amount of chlorotrifluoroethylene in the presence of a catalytic amount of $AlBr_3$ and, preferably, a solvent comprising $C_2F_4ClI$. The reaction is conducted at a temperature above 25° C. for a time sufficient to form the $CF_3CFClI$.

DETAILED DESCRIPTION OF THE INVENTION

The present invention is based on the unexpected discovery that the novel process described herein produces a better yield of $CF_3CFClI$ in a shorter time than known methods. Specifically, the inventors have discovered that the use of an $AlBr_3$ catalyst and elevated temperatures during the reaction of iodine, iodine pentafluoride and CTFE both increases the yield of the $CF_3CFClI$ and decreases the reaction time compared with prior art methods. This was particularly unexpected since the prior art does not teach the use of this catalyst in the reaction nor the use of elevated temperatures.

The reaction of iodine, iodine pentafluoride and CTFE as taught in the art is thought to proceed via the following equation and stoichiometry:

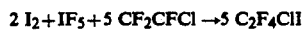

$$2\,I_2 + IF_5 + 5\,CF_2CFCl \rightarrow 5\,C_2F_4ClI$$

with the resultant product being a mixture of the isomers (or adducts) $CF_3CFClI$ and $CF_2ClCF_2I$. The art also teaches that varying yields of the total product (i.e., adduct mixture) and varying yields of the 2 possible adducts are obtained. Since $CF_3CFClI$ is the only adduct desirable for use in telomerization reactions, increased yield of this product is desirable. The inventors have discovered that when $AlBr_3$ is used as a catalyst and the reaction temperature is maintained as taught herein, the yield of crude product (i.e., the mixture of $CF_3CFClI$ & $CF_2ClCF_2I$) is generally in excess of 70% and often in excess of 80-90%. Likewise, the use of the catalyst and process herein results in a higher percentage of the product being the desired adduct (i.e., $CF_3CFClI$). For example, generally greater than about 60% of the product is the desired adduct and often the percentage is in excess of 70 or 80%. These yields are substantially higher than those obtained by prior art processes (e.g., Chambers et al. and Hauptschein et al. supra).

It can also be seen from the above reaction that when less than 2 moles of $I_2$ per mole of $IF_5$ are used the $I_2$ is nearly completely reacted. The inventors herein have found such a ratio to be preferable since residual $I_2$ can react with the CTFE to produce undesired by-products.

The inventors herein have also discovered that it is preferable to conduct this reaction in a solvent comprising $CF_3CFClI$. Yields of the desired product are, thereby, also generally increased.

The process of the present invention merely involves mixing $I_2$, $IF_5$, $AlBr_3$ and CTFE in an appropriate reaction vessel while regulating temperature for a time sufficient to form the $CF_3CFClI$. All of these materials are well known and commercially available. If desired, however, the reactants can be produced in-situ or in a separate reaction. For instance, the iodine pentafluoride may be produced by placing solid iodine in a reaction vessel and introducing fluorine gas as described in U.S. Pat. No. 3,367,745. The amount of $IF_5$ used in the process of this invention is generally not critical but it is preferred that it be used in an $I_2:IF_5$ molar ratio of less than about 3:1. preferably less than about 2:1. Generally, a molar ratio in the range of about 1:1.8 to about 1.95:1 is particularly preferred.

The aluminum bromide used herein can be made by the reaction of aluminum and bromine as described by Nicholson et al, in Inorg. Syn. 3, 30 (1950). Generally, it is used in the above reactions in an amount sufficient to catalyze the reaction of the $I_2$ with the $IF_5$. Typically, this amount is less than about 0.5 moles per mole of $I_2$ with amounts in the range of about 0.01 to 0.1 mole per mole $I_2$ being preferred.

The CTFE used herein is commercially available from, for instance, DuPont or Allied Corp. (Genetron 1113 ®). It is commercially produced by methods such as the dechlorination of 1,1,2 trichloro-1,2,2-trifluoroethane by vapor phase dehalogenation at 500°-600° C. or in the liquid phase using zinc in methanol. Although the amount of CTFE used in the above reaction is not critical, it is generally at least a stoichiometric amount, i.e., 5 moles CTFE per 2 moles of $I_2$. A stoichiometric excess (e.g., 5-25% molar excess) is often preferred to insure complete reaction.

The above reaction can be run in a solvent, if desired. The preferred solvent, if used, is $C_2F_4ClI$ which is also the reaction product of the present invention. It can be produced by the methods herein or, alternatively, it can be produced in smaller amounts by the method of Chambers et al. in J Chem. Soc., 3779 (1961), or Hauptschein et al. in J. Amer. Chem Soc. 83 (1961) 2383. It is generally used in an amount sufficient to dilute the above reactants to a desirable concentration.

The order of mixing the above ingredients in the reaction vessel is not critical. In a preferred method, however, the AlBr$_3$ catalyst is first mixed with a solvent, preferably C$_2$F$_4$ClI, under an inert atmosphere. Since this reaction is exothermic, the rate of addition must be controlled to avoid overheating, i.e., the temperature should generally not exceed 150° C. The resultant mixture is then added to a mixture of the I$_2$ and IF$_5$ in an inert reactor followed by the slow addition of the CTFE. Since this reaction is also exothermic, the mixture is generally cooled and the rate of addition is controlled to maintain the temperature less than about 150° C. After all of the CTFE has been added, the reactor is heated to a temperature above room temperature preferably in the range of about 40° to about 150° C. for a time sufficient to form the product. Generally, the reactor is heated between about ½ hour and about 10 hours, preferably 1-5 hours and more preferably about 2 hours. This is substantially quicker than by known methods which require several days for preparation.

Although the above process is preferred, alternative methods can also be used. For instance, the I$_2$, IF$_5$, AlBr$_3$ and solvent may be introduced consecutively into the reactor and then the CTFE slowly added while maintaining the appropriate temperature. After the reactants are added, the mixture is heated as above.

The product resulting from the above reaction can then be worked up by techniques known in the art. For instance, the telogen can be separated by pouring it into a Na$_2$S$_2$O$_5$-KOH solution, washing it with water and drying with CaSO$_4$.

the resultant liquid telogens are produced in yields of between 70 and 100% with yields of the desired adduct in the range of between about 65 and 100%. These telogens are useful for reacting with fluorinated olefins to produce a variety of telomers.

The following non-limiting examples are provided so that one skilled in the art may more readily understand the invention.

EXAMPLES 1-7

The following procedure was used to prepare the products listed in Table 1. The quantity of reactants is set forth in the Table except that 56 g (0.22 mole) of I$_2$ and 30 g (0.14 mole) of IF$_5$ were used in Examples 1 and 3-7 and 28 g of I$_2$ (0.11 mole) and 15 g (0.07 mole) of IF$_5$ were used in Example 2.

A magnetic stirring bar, I$_2$, IF$_5$ C$_2$F$_4$ClI and AlBr$_3$ were put in a 200 mL Hastalloy ® reactor. The reactor was cooled to −30° C. and the CTFE was introduced. The reactor was heated in an oil bath. At approximately room temperature enough iodine had been either dissolved or converted to a liquid product so the mixture could be stirred with a magnetic stirrer and the reaction began to exotherm. At the exotherm temperature listed in the table the reactor was cooled with a cold acetone bath. As the reaction proceeded the exotherm diminished. The reactor was then put back into the oil bath and heated at the temperature and for the time listed in the table. The reactor was cooled in an ice water bath to about 10° C. Excess CTFE was vented through a trap cooled in an ice water bath. The reactor was opened and the contents were poured into a solution of Na$_2$S$_2$O$_5$ hydrate (25 g) and KOH (5 g) in water (200 mL). The phases were separated to give the crude product. The crude product yield was calculated by subtracting the amount of product in the initial reaction mixture (i.e. that used as a solvent) from the amount of final product. The final product was then washed with distilled water two times to give the final product yield (the product was dried with CaSO$_4$ in some of the runs). The results are provided in Table 1.

TABLE 1

| | Catalyst (g) | | CTFE | C2F4ClI | Synthesis of C$_2$F$_4$ClI Exotherm | Temp/Time | Crude Prod | Purity | Mole % |
|---|---|---|---|---|---|---|---|---|---|
| Ex | AlBr3 | Al | (g)$^a$ | (g)$^b$ | Max °C./Bar | (°C.)/(hrs) | Yield (%) | (%) | C$_2$F$_4$ClI |
| 1 | 3.4 | 2 | 94 | 27 | 150/40$^c$ | 25/16 | 40 | 73 | 66 |
| 2$^d$ | 1.4 | 0.25 | 75 | 50 | 96/12 | 104/16 | 77 | 91 | 67 |
| 3 | 2.7 | 0.25 | 104 | 43.4 | 125/20$^e$ | 100/3 | 103 | 89 | 79 |
| 4 | 2.1 | — | 91 | 46 | 100/15$^f$ | 60/2 | 72 | 96 | 65 |
| 5 | 2.7 | — | 133 | 40 | 81/10$^g$ | 80/16 | 76 | 96 | 69 |
| 6 | 2.8 | 0.25 | 87 | 46 | 98/15$^h$ | 100/3 | 92 | 96 | 67 |
| 7 | 2.6 | — | 101 | 40 | 104/18$^i$ | 100/3 | 100$^j$ | 80 | 87 |

$^a$Theoretical CTFE (0.58 mole CTFE; 0.14 mole IF$_5$; and 0.22 mole I$_2$) is 67 g.
$^b$Used as solvent
$^c$Reaction Exothermed from 70° C. At 150°C. the reactor was removed from the oil bath and temperature dropped to 125° C.
$^d$Half reaction (0.28 mole). Residue (5 g) was C$_2$F$_4$ClI (26%) and higher boiling by-products (59%)
$^e$Exotherm began at 40° C. Reactor taken from bath at 80° C.
$^f$Exotherm began at 40° C. Reactor placed in cold water bath when temperature reached 80° C.
$^g$Exotherm was very slow and reactor was not removed from bath.
$^h$Exotherm began at 35° C. At 75° C. the reactor was placed in a cold acetone bath.
$^i$Reactor was placed in cold acetone bath (−30° C.) at 60° C.
$^j$Yields of 100% and higher are observed because some higher boiling by-products are formed.

EXAMPLES 8-14

The following procedure was used to prepare the products listed in Table 2. The quantity of reactants is set forth in the Table.

A 3-necked flask equipped with a nitrogen atmosphere, reflux condenser and magnetic stirrer is charged with C$_2$F$_4$ClI. The aluminum bromide is slowly added to the flask and a strong exothermic reaction occurs. The I$_2$ and IF$_5$ is charged into a Hastalloy ® reactor and the catalyst mixture added to it. Air in the reactor is then removed by applying a vacuum for 30-60 seconds.

The reactor is warmed to about 40°-50° C. and the flow of CTFE gas started at a rate of about 1 to 3 g per minute. The reaction is exothermic and cooling must initially be applied to maintain the desired temperature. As the reaction proceeds the reaction temperature drops and cooling may be discontinued. After all of the CTFE has been added to the reactor, the mixture is heated at the temperature listed in the table for about 2 hours. The reaction mixture is then worked up as in Examples 1–7 ($Na_2S_2O_5$ hydrate and KOH). The results are provided in Table 2.

TABLE 2

| Ex | $I_2$ | $IF_5$ | Weight of Reagents (g) $C_2F_4ClI$ | CTFE | $AlBr_3$ | Temp °C. | Yield of Crude Prod (%) | Mole % $CF_3CFClI$ by GC* | By $^{19}F$ NMR |
|----|-----|------|-------|------|-------|------|-----|------|------|
| 8  | 56  | 33.3 | 0     | 100  | 2.5   | 100  | 83  | 62   | 58   |
| 9  | 56  | 31   | 90    | 100  | 2.5   | 75–80| 77  | 59   | 55   |
| 10 | 84  | 46.5 | 135   | 130  | 3.75  | 80   | 93  | 81   | 77   |
| 11 | 146 | 81   | 157   | 216  | 6.2   | 50–80| 90  | 62   | 55   |
| 12 | 185 | 103  | 182   | 278  | 7.9   | 50   | 100 | 80   | 77   |
| 13 | 185 | 103  | 190   | 282  | 7.9   | 50   | 98  | 66   | 63   |
| 14 | 185 | 103  | 190   | 270  | 7.9   | 50   | 98  | 85   | 84   |

*30 meter Carbowax ® Capillary Column

EXAMPLES 15–18 (COMPARATIVE)

The following Examples are provided to compare the results of the present invention with that of Hauptschein et al. supra. The procedure is set forth below and the quantity of reactants and products are listed in Table 3.

A 200 mL reactor was charged with $I_2$, aluminum foil and $AlI_3$. $IF_5$ was added to the reactor resulting in an exotherm. The reactor was then heated as indicated in the table (Step 1). The reactor was cooled to −50° C. and the CTFE was slowly introduced. The reactor was warmed and stirred to the temperature/time set forth in the table (Step 2). The reaction mixture was worked up with $Na_2S_2O_5$ and washed with water. The results are provided in Table 3.

TABLE 3

| Ex | Catalyst (g) $AlI_3$ | Al | $CTFE^a$ (g) | Step 1 Temp/Time (°C./hrs) | Comparative Step 2 Temp/Time (°C./hrs) | Yield of Crude Prod (%) | Purity (%) | Mole % $CF_3CFClI$ |
|----|-----|---|------|---------|---------|----|----|----|
| 15 | 2   | 2 | 77.4 | 140/1   | 25/16   | 18 | 72 | 60 |
| 16 | 2   | 2 | 98   | 130–35/2.5$^b$ | 28/48$^b$ | 68 | 72 | 65 |
| 17$^c$ | 3 | 3 | 118 | 130/2.5$^d$ | 25/12 | 1 | — | — |
| 18 | 2   | 2 | 99   | 130–40/2.5$^e$ | 25/48 | 31 | — | 63 |

$^a$All reactions except Example 17 used 0.22 mole of $I_2$ and 0.12 mole of $IF_5$. Theory for CTFE is 0.56 mole.
$^b$Exotherm to 151° C. in Step 1 and 30° C. (reaction cooled to keep at 30° C.) in Step 2.
$^c$Reaction scaled up by 50%
$^d$Exotherm to 180° C. in Step 1, no exotherm observed in Step 2.
$^e$No exotherm observed.

That which is claimed is:

1. A method of making $CF_3CFClI$ comprising: reacting a mixture comprising iodine, iodine pentafluoride and at least a stoichiometric amount of chlorotrifluoroethylene in the presence of a catalytic amount of $AlBr_3$ at a temperature above 25° C. for a time sufficient to form the $CF_3CFClI$.

2. The method of claim 1 wherein the molar ratio of iodine to iodine pentafluoride is less than about 2:1.

3. The method of claim 1 wherein the molar ratio of iodine to iodine pentafluoride is in the range of about 1:1.8 to about 1.95:1.

4. The method of claim 1 wherein the reaction is conducted in a solvent comprising $C_2F_4ClI$.

5. The method of claim 1 wherein the $AlBr_3$ is present in a range of about 0.01 mole to 0.1 mole $AlBr_3$ per mole of $I_2$.

6. The method of claim 1 wherein the chlorotrifluoroethylene is present in about a 5–25 mole % stoichiometric excess.

7. The method of claim 1 wherein the temperature of reaction is between about 40° and about 150° C.

8. The method of claim 1 wherein the time of reaction is in the range of about 1 to about 5 hours.

* * * * *